US009164064B2

(12) United States Patent
Couse et al.

(10) Patent No.: US 9,164,064 B2
(45) Date of Patent: Oct. 20, 2015

(54) FLAW DETECTION METHOD AND APPARATUS FOR FUEL CELL COMPONENTS

(71) Applicant: Bloom Energy Corporation, Sunnyvale, CA (US)

(72) Inventors: Stephen Couse, Sunnyvale, CA (US); Tulin Akin, Sunnyvale, CA (US)

(73) Assignee: BLOOM ENERGY CORPORATION, Sunnyvale, CA (US)

( * ) Notice: Subject to any disclaimer, the term of this patent is extended or adjusted under 35 U.S.C. 154(b) by 260 days.

(21) Appl. No.: 13/859,892

(22) Filed: Apr. 10, 2013

(65) Prior Publication Data
US 2013/0269436 A1 Oct. 17, 2013

Related U.S. Application Data

(60) Provisional application No. 61/749,984, filed on Jan. 8, 2013, provisional application No. 61/623,841, filed on Apr. 13, 2012.

(51) Int. Cl.
*G01N 29/12* (2006.01)
*G01N 29/44* (2006.01)

(52) U.S. Cl.
CPC .......... *G01N 29/12* (2013.01); *G01N 29/4427* (2013.01); *G01N 2291/0289* (2013.01); *G01N 2291/102* (2013.01)

(58) Field of Classification Search
CPC ............ G01N 29/12; G01N 2291/102; G01N 2291/0289; G01N 29/4427
USPC .......................................... 73/582, 579, 602
See application file for complete search history.

(56) References Cited

U.S. PATENT DOCUMENTS

| | | | |
|---|---|---|---|
| 5,257,544 A * | 11/1993 | Khuri-Yakub et al. | 73/579 |
| 5,495,763 A * | 3/1996 | Rhodes et al. | 73/579 |
| 6,426,161 B1 | 7/2002 | Cisar et al. | |
| 6,517,879 B2 * | 2/2003 | Capodieci | 426/238 |
| 6,599,651 B1 | 7/2003 | Saitou et al. | |
| 6,880,379 B2 * | 4/2005 | Hedberg et al. | 73/12.01 |
| 8,802,331 B2 * | 8/2014 | Herchen et al. | 429/535 |

(Continued)

FOREIGN PATENT DOCUMENTS

| | | |
|---|---|---|
| JP | 2000-285934 A | 10/2000 |
| JP | 2007-042406 A | 2/2007 |
| KR | 10-2010-0109253 A | 10/2010 |

OTHER PUBLICATIONS

International Search Report and Written Opinion received in connection with international application No. PCT/US2013/035895, mailed Jul. 25, 2013.
International Preliminary Report on patentability received in connection with international application No. PCT/US2013/035895, mailed Oct. 23, 2014.
International Search Report & Written Opinion, PCT/US2011/062328, Aug. 1, 2012.
Huth et al., "Lock-in IR-Thermography—a novel tool for material and device characterization," Solid State Phenomena 82-84, pp. 741-746 (2002).

(Continued)

*Primary Examiner* — J M Saint Surin
(74) *Attorney, Agent, or Firm* — The Marbury Law Group PLLC

(57) ABSTRACT

Various embodiments provide systems and methods for detecting defects in components of a fuel cell. Embodiment methods and systems include directing acoustic energy into the component, detecting acoustic energy from the component, analyzing a characteristic of the detected acoustic energy, and based on the analyzing, determining the presence or absence of a defect in the component.

2 Claims, 13 Drawing Sheets

(56) References Cited

U.S. PATENT DOCUMENTS

| | | |
|---|---|---|
| 2005/0142431 A1 | 6/2005 | Shimomura et al. |
| 2006/0228613 A1 | 10/2006 | Bourgeois et al. |
| 2008/0131739 A1* | 6/2008 | Badding et al. .................. 429/13 |
| 2010/0225339 A1* | 9/2010 | Fujita et al. .................. 324/699 |
| 2012/0135337 A1 | 5/2012 | Herchen et al. |
| 2013/0230072 A1 | 9/2013 | Couse et al. |

OTHER PUBLICATIONS

Low Cost, High Efficiency Reversible Fuel Cell (and Electrolyzer) Systems, Proceedings of the 2001 DOE Hydrogen Program Review NREL/CP-570-30535.

* cited by examiner

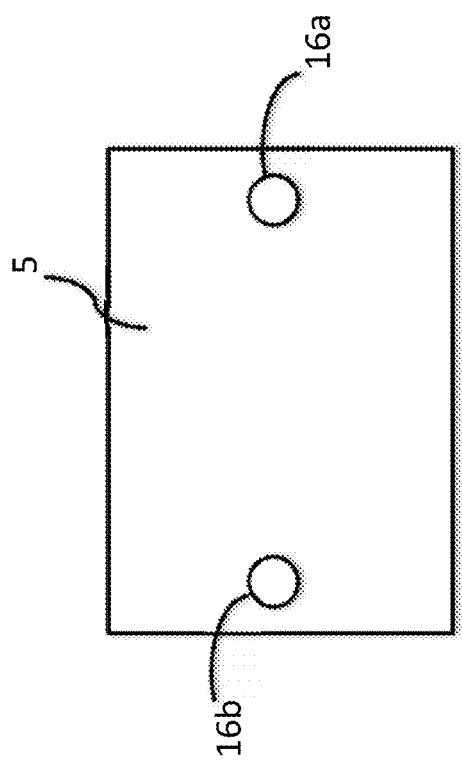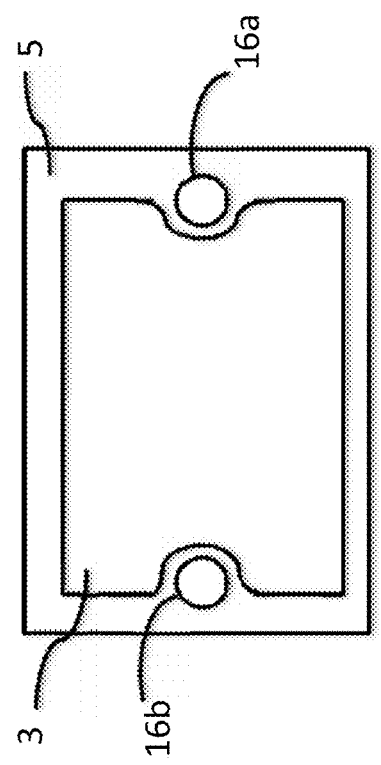
FIG. 2A
FIG. 2B

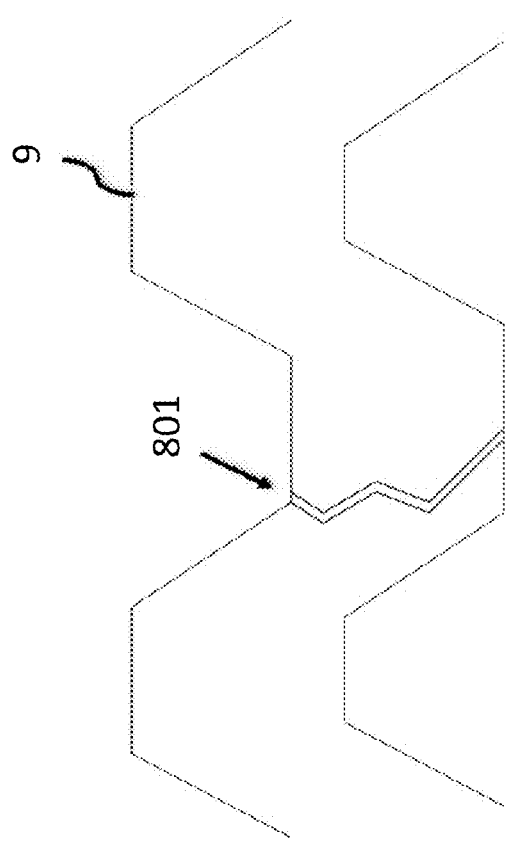
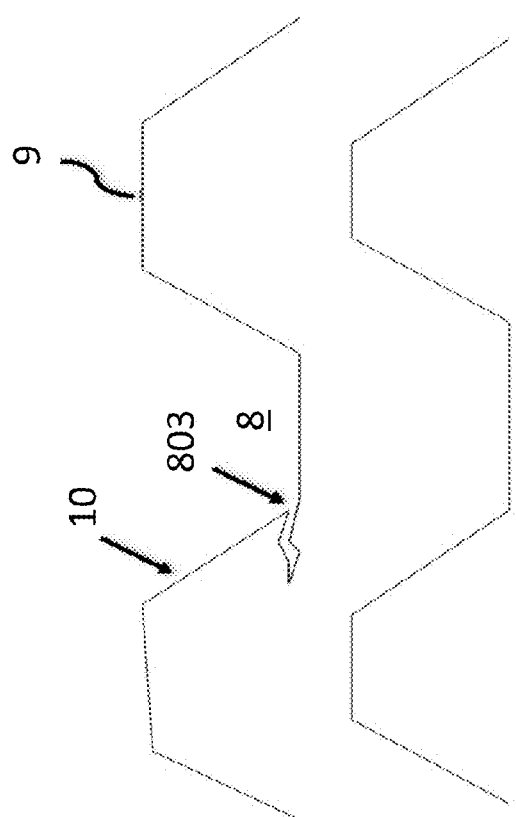
FIG.8A
FIG.8B

FLAW DETECTION METHOD AND APPARATUS FOR FUEL CELL COMPONENTS

RELATED APPLICATION

This application claims the benefit of priority to U.S. Provisional Application No. 61/749,984, entitled "Flaw Detection Method and Apparatus for Fuel Cell Components," filed on Jan. 8, 2013, and to U.S. Provisional Application No. 61/623,841, entitled "Flaw Detection Method and Apparatus for Fuel Cell Components," filed on Apr. 13, 2012. The entire contents of these applications are incorporated by reference herein.

BACKGROUND

In a high temperature fuel cell system, such as a solid oxide fuel cell (SOFC) system, an oxidizing flow is passed through the cathode side of the fuel cell while a fuel flow is passed through the anode side of the fuel cell. The oxidizing flow is typically air, while the fuel flow can be a hydrocarbon fuel, such as methane, natural gas, pentane, ethanol, or methanol. The fuel cell, operating at a typical temperature between 750° C. and 950° C., enables the transport of negatively charged oxygen ions from the cathode flow stream to the anode flow stream, where the ion combines with either free hydrogen or hydrogen in a hydrocarbon molecule to form water vapor and/or with carbon monoxide to form carbon dioxide. The excess electrons from the negatively charged ion are routed back to the cathode side of the fuel cell through an electrical circuit completed between anode and cathode, resulting in an electrical current flow through the circuit.

In order to optimize the operation of SOFCs, the various components of the system, such as the electrolyte, the anode and cathode electrodes and interconnects should be precisely manufactured and generally free of defects.

SUMMARY

Embodiments include methods for testing a fuel cell component that includes directing acoustic energy into the component, detecting acoustic energy from the component, analyzing a characteristic of the detected acoustic energy, and based on the analyzing, determining a presence or absence of a defect in the component.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIG. 2A is a plan view of an electrolyte of a fuel cell.

FIG. 2B is a plan view of an electrolyte and an electrode of a fuel cell.

FIGS. 8A and 8B illustrate different types of crack defects in an interconnect for a fuel cell system.

DETAILED DESCRIPTION

Figure 1A:
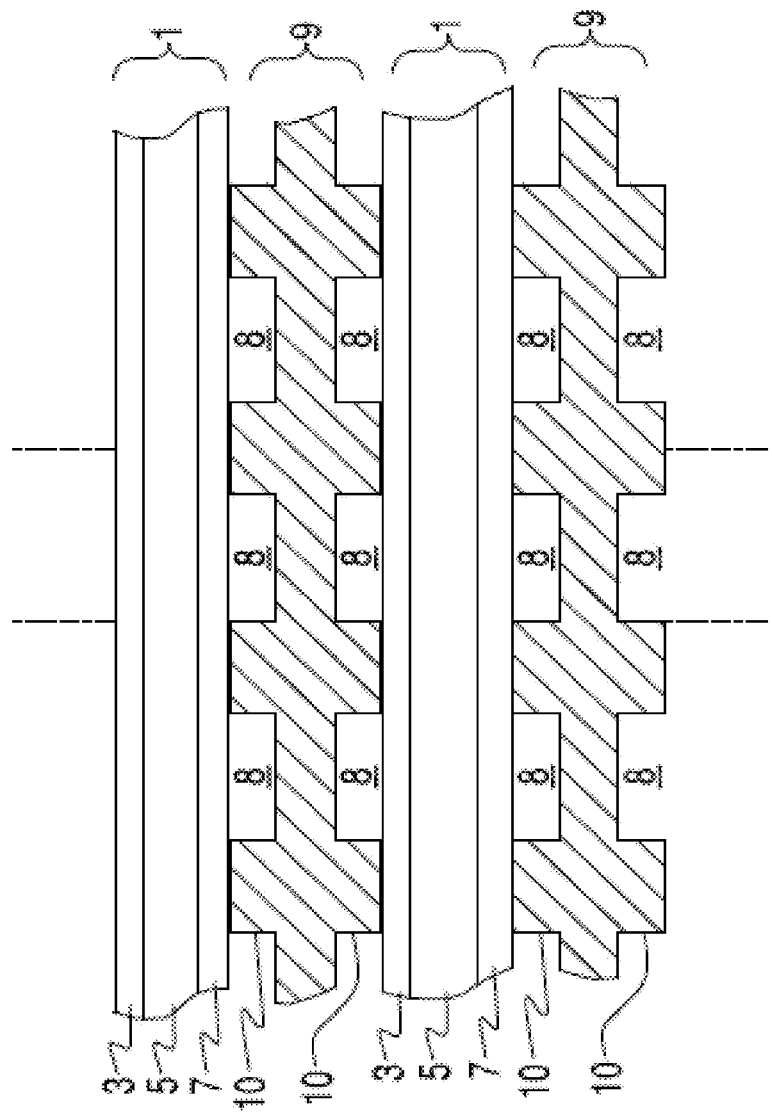
FIG. 1A illustrates a side cross-sectional view of a SOFC stack.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

In one aspect, the present invention provides accurate, rapid and non-destructive techniques for detecting defects in fuel cell components, which are expected to greatly improve the fabrication process for solid oxide fuel cell devices. It is anticipated that the present detection technique will result in lower costs for these devices, since defective components and cells can be more easily identified and removed at an earlier stage of production and/or use. Furthermore, the present defect detection methodology should help lower production costs of many fuel cell systems, since the current labor-intensive and time-consuming inspection processes can now be avoided.

FIG. 1 illustrates a SOFC stack in which each SOFC 1 comprises a cathode electrode 7, a solid oxide electrolyte 5, and an anode electrode 3. Fuel cell stacks are frequently built from a multiplicity of SOFC's 1 in the form of planar elements, tubes, or other geometries. Fuel and air has to be provided to the electrochemically active surface, which can be large.

The gas flow separator 9 (referred to as a gas flow separator plate when part of a planar stack), containing gas flow passages or channels 8 between ribs 10, separates the individual cells in the stack. The gas flow separator plate separates fuel, such as a hydrocarbon fuel, flowing to the fuel electrode (i.e. anode 3) of one cell in the stack from oxidant, such as air, flowing to the air electrode (i.e. cathode 7) of an adjacent cell in the stack. At either end of the stack, there may be an air end plate or fuel end plate (not shown) for providing air or fuel, respectively, to the end electrode.

Frequently, the gas flow separator plate 9 is also used as an interconnect which electrically connects the anode or fuel electrode 3 of one cell to the cathode or air electrode 7 of the adjacent cell. In this case, the gas flow separator plate which functions as an interconnect is made of or contains electrically conductive material. FIG. 1 shows that the lower SOFC 1 is located between two interconnects 9.

Figure 1B:
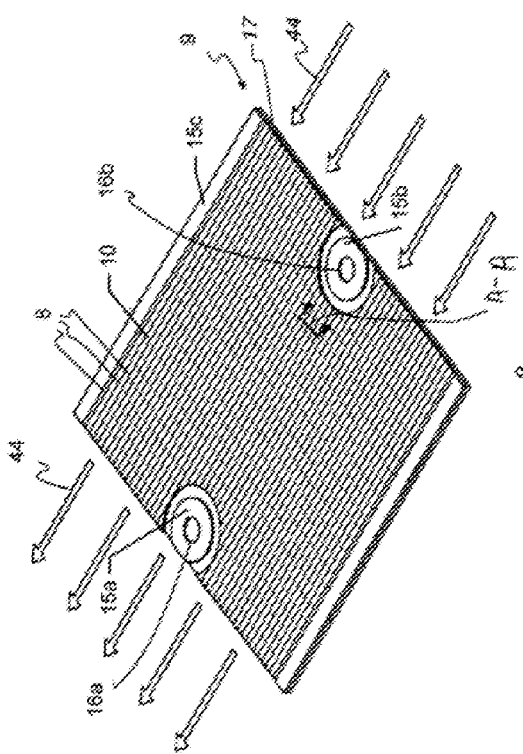
FIGS. 1B and 1C show, respectively, top and bottom views of an interconnect for a SOFC stack.
Figure 1C:
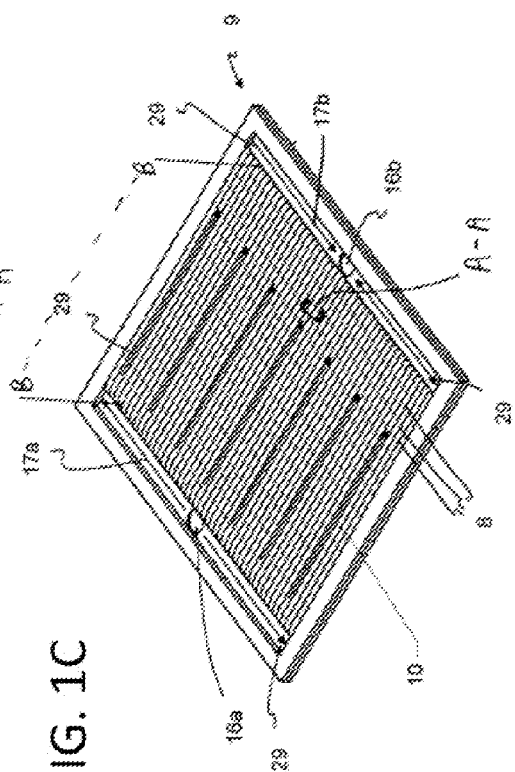

FIGS. 1B and 1C show, respectively, top and bottom views of an interconnect 9. The portions of interconnect 9 shown in side cross-section in FIG. 1A are provided along lines A-A in FIGS. 1B and 1C. The interconnect 9 contains gas flow passages or channels 8 between ribs 10. The interconnect 9 in this embodiment includes at least one riser channel 16a for providing fuel to the anode-side of the SOFC 1, as illustrated by arrow 29. The riser channel 16a generally comprises a fuel inlet riser opening or hole that extends through at least one layer of the fuel cells and interconnects in the stack. As illustrated in FIG. 1C, the fuel can flow through the inlet riser channel 16a to the anode-side of each fuel cell. There, the fuel can collect in an inlet plenum 17a (e.g., a groove in the interconnect's surface), then flow over the fuel cell anode 3 through gas flow channels 8 formed in the interconnect 9 to an outlet plenum 17b and then exit through a separate outlet riser channel 16b.

The cathode side, illustrated in FIG. 1B, can include gas flow passages or channels 8 between ribs 10 which direct air flow 44 over the cathode electrode of the fuel cell. Seals 15a, 15b can seal the respective risers 16a, 16b on the cathode-sides of the interconnect and fuel cell to prevent fuel from reaching the cathode electrode of the fuel cell. The seals may have a donut or hollow cylinder shape as shown so that the risers 16a, 16b extend through the hollow middle part of the respective seals 15a, 15b. The seals 15a, 15b can include a elevated top surface for contacting against the flat surface of the adjacent SOFC 1. A peripheral seal 15c can seal the anode-sides of the interconnect and fuel cell to prevent air from reaching the anode electrode of the fuel cell.

FIG. 2A is a plan view of a solid oxide electrolyte 5. The electrolyte 5 may comprise a stabilized zirconia, such as scandia stabilized zirconia (SSZ) or yttria stabilized zirconia (YSZ). Alternatively, the electrolyte 5 may comprise another ionically conductive material, such as a doped ceria. In this embodiment, the electrolyte 5 has a planar geometry, although it will be understood that other geometries, such as a tubular geometry, could be utilized. Riser channel openings 16a, 16b, which in this embodiment comprise circular holes, extend through the electrolyte 5. The riser channels 16a, 16b generally comprise fuel inlet and outlet openings that extend through at least one layer of the fuel cells. The riser channels 16a, 16b can extend through multiple electrolyte layers 5 and interconnects 9 between the electrolyte layers in a fuel cell stack. Fuel can flow through the inlet riser channel 16a to the anode-side of each fuel cell. There, the fuel flows over the fuel cell anode 3 via gas flow channels 8 formed in the gas flow separator/interconnect plate 9, and then exits through separate outlet riser channel 16b.

In FIG. 2B, an anode (e.g., fuel) electrode 3 is shown covering part of a first major surface of the electrolyte 5. A cathode (e.g., air) electrode 7 (not shown) can cover part of the second major surface on the opposite side of the electrolyte 5.

The SOFC 1 in this embodiment is configured for a stack that is internally manifolded for fuel and externally manifolded for air. Thus, the stack is open on the air inlet and outlet sides. Alternatively, the SOFC 1 may be configured for a stack which is internally manifolded for both air and fuel. In this case, the electrolyte would contain additional air inlet and outlet openings. Alternatively, the SOFC 1 may be externally manifolded for air and fuel.

The various fuel cell components must be precisely manufactured to maximize fuel cell efficiency. The fuel cell components must also be substantially free of defects, including small cracks in the components and/or delamination of layered components, such as ink printed electrodes 3, 7 on the electrolyte 5.

Cracks and other defects in a solid oxide fuel cell reduce the mechanical stability of the cell and may lead to the breakage of the electrolyte or the fuel cell. In order to manufacture high-quality fuel cells, it would be desirable to utilize an in-line inspection technique that can quickly and accurately identify fuel cell defects in a non-destructive manner. One way to reduce fabrication costs is by reducing the substrate (e.g., electrolyte or anode for electrolyte or anode supported cells, respectively) thickness, and the mechanical stability of the wafer is becoming an even more important consideration.

In the fuel cell electrolyte, small cracks which may be invisible to the naked eye can cause fuel leaks from the anode to the cathode side of the cell in use. The resulting leak can cause damage to other components of the fuel cell assembly. The fuel riser openings can cause stress concentrations in the ceramic electrolyte and many cracks are found in the vicinity of these openings. Current inspection techniques are costly, slow and often do not effectively identify cracks. In some cases, the inspection technique itself can cause damage to the electrolyte.

Delamination of the electrodes from the electrolyte is another problem that can reduce the efficiency of the fuel cell and may lead to overall stack performance issues. One way of reducing costs is by decreasing the electrode thickness. Thus, the effectiveness of the electrode sintering is becoming more important. Current inspection techniques for detecting electrode delamination are costly and slow. Thus, it would be desirable to provide a rapid and accurate technique for detecting delamination of an electrode layer before fuel cell stack assembly.

Figure 3:
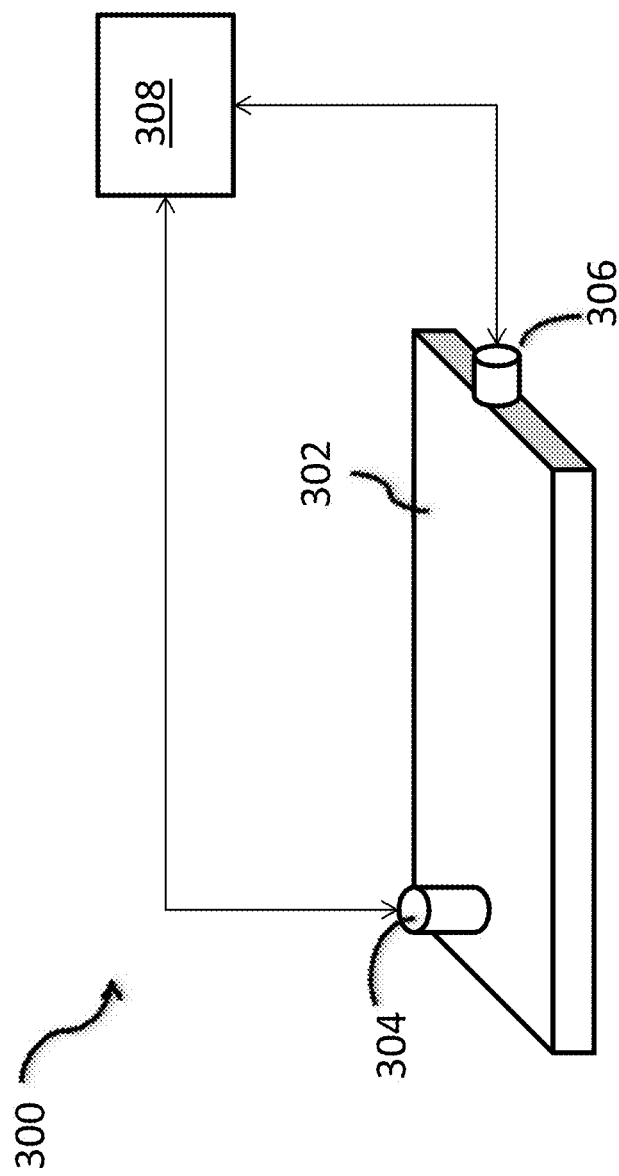
FIG. 3 illustrates a fuel cell component and an ultrasound testing apparatus configured to detect defects in the component.

FIG. 3 schematically illustrates a system 300 for detecting defects in a component of a fuel cell. In one embodiment, the system 300 includes a source of acoustic energy 304, which may be a first transducer that contacts a fuel cell component 302 and is configured to direct acoustic energy, such as ultrasound energy, into the component 302. The system 300 in this embodiment further includes a detector of acoustic energy 306, which may be a second transducer that contacts the fuel cell component 302. The detector 306 can be configured to detect acoustic energy, such as ultrasound energy, which passes through the component 302. In some embodiments, the fuel cell component 302 can be an electrolyte plate or layer, including raw electrolyte material. In some embodiments, the fuel cell component 302 can be an electrolyte plate or layer having one or more electrodes provided on the electrolyte, and can be a finished cell, such as SOFC 1 shown in FIGS. 1 and 2B. In some embodiments, a single transducer can serve as both the source of acoustic energy and as the detector, and can for instance direct acoustic energy into the fuel cell component 302 and detect reflected acoustic energy from the component 302.

In one embodiment, a controller 308 can be electronically coupled to the source 304 and detector 306, as shown in FIG. 3. Controller 308 can be a logic device (e.g., computer) and can include a memory and a processor coupled to the memory, wherein the processor can be configured with processor-executable instructions for performing various functions. In one embodiment, the controller 308 is configured to control the operation of the source of acoustic energy 304 to cause the source 304 to direct acoustic energy such as ultrasound energy to component 302. In some embodiments, the controller 308 can be configured to control one or more characteristics of the acoustic energy generated by the transducer, such as the amplitude, pulse duration and/or rate and frequency characteristics of the acoustic energy directed into component 302. The controller 308 can also be configured to receive an electronic signal representation of the acoustic energy detected at the detector 306, and to analyze the received signal to determine the existence of defects in the fuel cell component 302.

Figure 4:
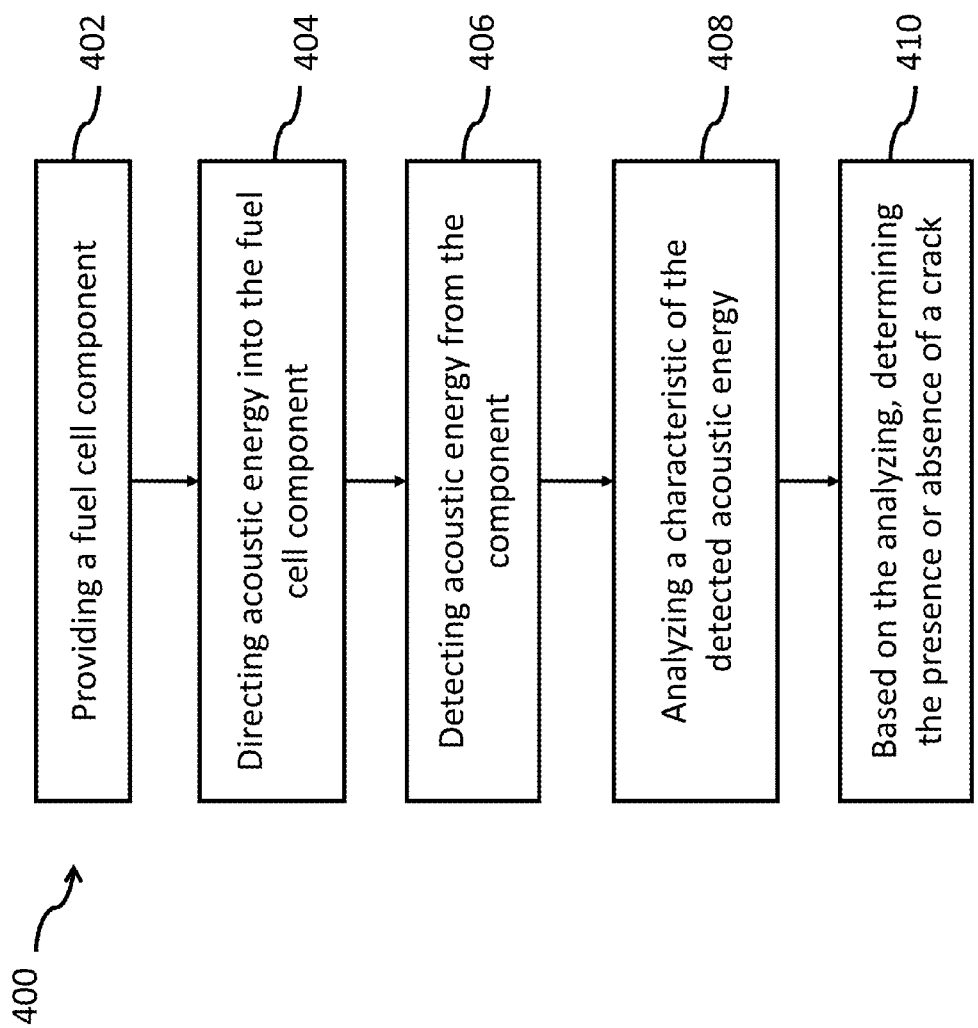
FIG. 4 is a process flow diagram illustrating an embodiment method for detecting cracks in a fuel cell component by measuring an induced ultrasound waveform from the component.

FIG. 4 illustrates an embodiment method 400 for detecting cracks in a fuel cell component. In embodiments, the method 400 can be performed using the system 300 as shown in FIG. 3. In step 402, a fuel cell component is provided. As discussed above, the fuel cell component can be the bare unprocessed electrolyte material. In other embodiments, the fuel cell component can be a partially or fully processed electrolyte, and can be coated with one or more electrodes. In one preferred embodiment, the fuel cell component is a finished fuel cell comprising an electrolyte, an anode electrode and a cathode electrode.

In step 404, acoustic energy is directed into the fuel cell component. The acoustic energy can be generated by a source of acoustic energy, such as source 304 shown in FIG. 3. The acoustic energy can be one or more short pulses (e.g., "pings") of acoustic energy generated by a transducer. In various embodiments, the ping can be an ultrasound signal. The frequency or frequency range of the acoustic energy can be selected to stimulate a known resonance frequency of the component. The energy and/or frequency of the acoustic pulse can be chosen to stimulate a resonance response of the component without causing damage to the component. For example, acoustic pulses in the kHz range may be unlikely to damage a typical fuel cell component. In step 406, acoustic energy from the fuel cell component is detected. The acoustic energy can be detected by a detector of acoustic energy, such as detector 306 shown in FIG. 3. In one embodiment, a probe transducer that can be in contact with the fuel cell component detects the acoustic energy. The detected acoustic energy can be an ultrasonic waveform induced in the component in response to ultrasound energy being directed into the component at step 404. The detected acoustic signal can be converted to an electronic signal by the transducer. The electronic signal can be sent to suitable processing device, such as controller 308 shown in FIG. 3, to be analyzed.

In step 408, a characteristic of the detected acoustic energy is analyzed, and based on the analysis, the presence or absence of a crack in the fuel cell component is determined in step 410. In various embodiments, the analyzing step 408 can comprise comparing the induced waveform from the component detected in step 404 with a waveform from a known "good" component (i.e., a component that is free or substantially free of cracks). Cracked electrolytes/fuel cells will produce a unique waveform that is repeatable. This uniqueness can be used to determine the presence or absence of a crack in the component being tested.

In various embodiments, the analyzing step 408 can comprise determining if the acoustic response of the component at a known resonance frequency is damped. A damping of the resonance response, which can be detected as a reduction in amplitude and/or as a shift in the resonance frequency relative to resonance response of a typical reference defect-free component, can be indicative of a crack in the component being tested. In various embodiments, a maximum deviation of the detected response from the expected or reference resonance response of a normal component can be set. The maximum deviation value(s) can be stored in a lookup table. Components with a greater than maximum deviation in their detected responses can be determined to have cracks at step 410, and can be rejected from a fabrication process. In some embodiments, the detected response can be compared to a statistical distribution of resonance response characteristics of a plurality of components.

In various embodiments, the method 400 of FIG. 4 enables accurate, high-throughput and non-destructive testing of fuel cell components to identify cracks in the components. In preferred embodiments, the method 400 provides rapid detection of cracks in fuel cell components, including electrolytes, and the testing method generally takes less than about 5 seconds to complete, and more particularly less than about 2 seconds to complete for each component tested.

Figure 5:
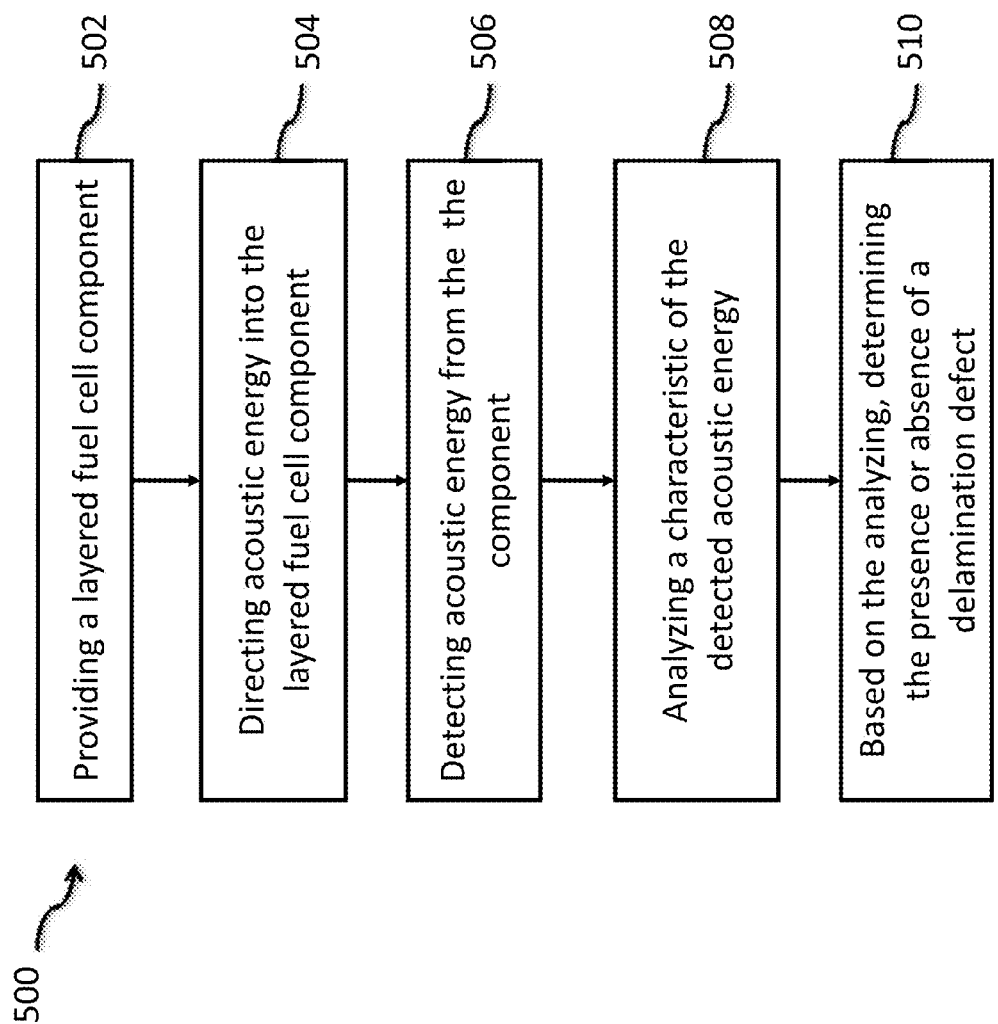
FIG. 5 is a process flow diagram illustrating an embodiment method for detecting delamination of a layered fuel component by measuring an induced ultrasound waveform from the component.

The system 300 of FIG. 3 can be used to detect delamination of a layered component, such as a delamination of one or both electrode layer(s) 3, 7 on an electrolyte 5, as shown in FIGS. 1 and 2B. FIG. 5 is a process flow diagram illustrating an embodiment method 500 for detecting delamination defects in a fuel cell component using acoustic energy. In step 502, acoustic energy, which can be ultrasound energy, is directed into the layered component (e.g., electrolyte 5 having one or both electrodes 3, 7 on opposite sides), as described above, and in step 504, the acoustic energy from the component is detected. In step 508, a characteristic of the detected acoustic energy is analyzed, and based on the analysis the presence or absence of a delamination defect can be determined in step 510.

Delamination defects in a layered component, which can be the result of an under-sintered electrode layer, produce a unique waveform in the detected acoustic energy that is repeatable. Thus, the waveform of the component being tested can be compared to a waveform from a normal (i.e., well-sintered, non-delaminated) reference cell to determine the presence or absence of a delamination defect. In various embodiments, the analyzing step 508 can comprise determining if the acoustic response of the layered component at a known resonance frequency is damped. A damping of the resonance response, which can be detected as a reduction in amplitude and/or as a shift in the resonance frequency relative to resonance response of a typical reference defect-free layered component, can be indicative of a delamination defect in the layered component being tested. In various embodiments, a maximum deviation of the detected response from the expected or reference resonance response of a normal layered component can be set. The maximum deviation value(s) can be stored in a lookup table. Layered components with a greater than maximum deviation in their detected responses can be determined to have delamination defects at step 510, and can be rejected from a fabrication process. In some embodiments, the detected response can be compared to a statistical distribution of resonance response characteristics of a plurality of components.

Acoustic energy can be applied to the layered component so that no damage is caused to the component. In embodiments, the method 500 takes generally less than about 5 seconds per component, and more particularly less than about 2 seconds to test each component.

Further embodiments may include non-destructive methods for testing a fuel cell component by active thermography. A fuel cell component, which may be bare unprocessed electrolyte material, or a partially or fully processed electrolyte, which can be coated with one or more electrodes (e.g., a finished cell), may be stimulated by one or more types of energy, such as ultrasound, induction (i.e., inductive heating), or optical energy (e.g., ultraviolet, visible, and/or infrared radiation), and the thermal response of the fuel cell component may be observed. Defects in the fuel cell component may be detected based on irregularities in the observed thermal response.

Active thermography differs from passive thermography in that an energy source is used to produce a thermal contrast between the test object and its surroundings. For example, a fuel cell component may be in thermal equilibrium with the background environment. After stimulating the fuel cell component with energy, the component releases heat to reestablish thermal equilibrium. This release of heat may be observed spatially (i.e., across the component) and temporally (i.e. over time, such as an infrared video or a series of pictures). Various algorithms may be used to determine defects based on this heat imaging. For example, a crack, a void, an impurity, or a delaminated coating (e.g., a cathode or anode electrode coating on an electrolyte) may release more heat or at a different rate than a defect free fuel cell component.

Figure 6:
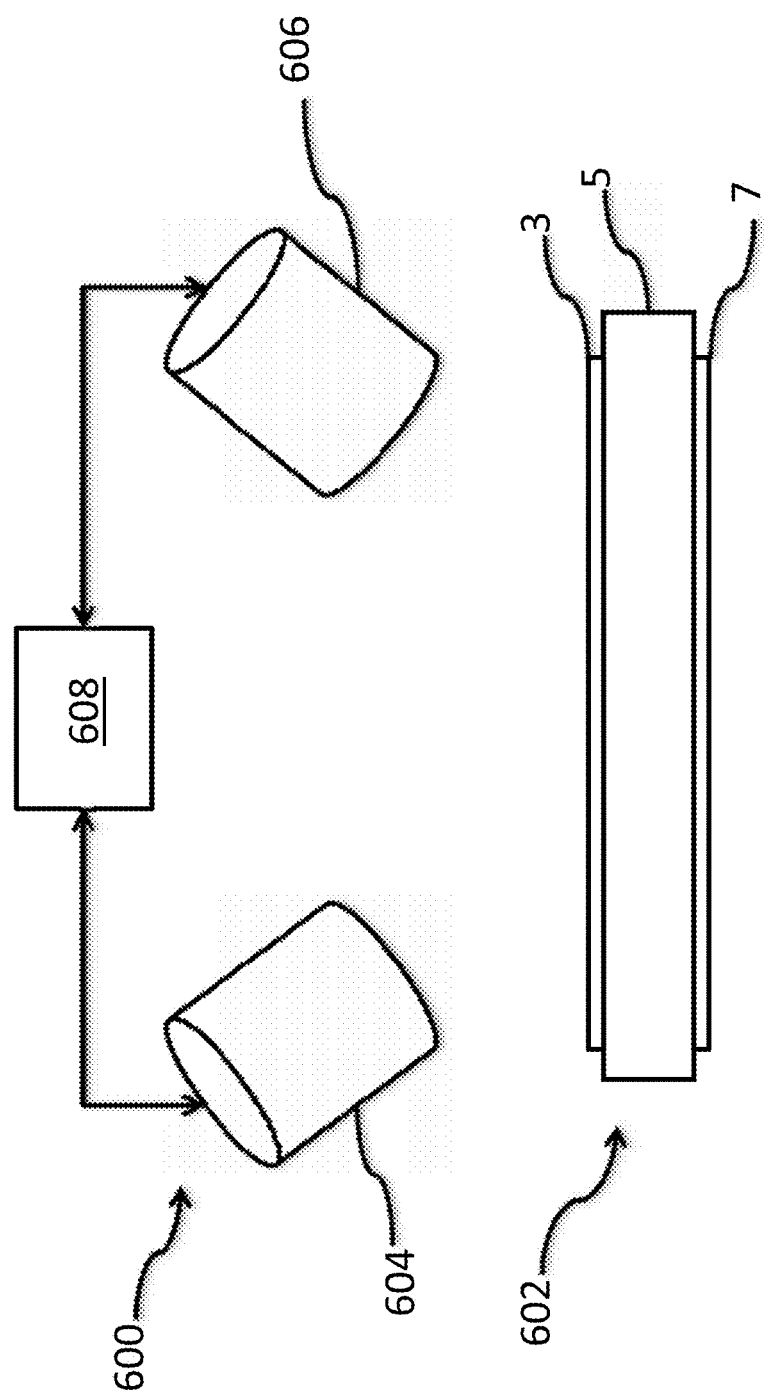
FIG. 6 illustrates a fuel cell component and a testing apparatus for detecting a delamination defect in the component by measuring a thermal response of the component to optical radiation energy directed at the component.

FIG. 6 schematically illustrates an embodiment system 600 for using active thermography to test fuel cell components. In one embodiment, the system 600 may be used for detecting delamination defects in layered components, including layered components of a fuel cell. The system 600 in this embodiment includes at least one source of optical energy 604 that is configured to direct optical radiation energy (e.g., ultraviolet, visible or infrared radiation, preferably infrared radiation) at a fuel cell component 602. The optical energy delivered to the fuel cell component 602 may be sufficient to cause a measurable temperature increase over at least a portion of the component 602 (e.g., 1-2 deg.C.) without causing damage to the component 602. Optical energy (e.g., radiation) may be pulsed or continuous. The source 604 can be, for example, a flashlamp, halogen lamp, LED, laser source, etc. In one embodiment, the source 604 can be a high-power, high-frequency photography lamp. The system 600 also includes at least one detector of thermal energy 606, which may be an infrared camera or infrared photodetector, for detecting a thermal response of the fuel cell component 602. The source 604 and detector 606 can be integrated into the same housing/device.

The fuel cell component 602 may be a finished cell, such as SOFC 1 shown in FIGS. 1 and 2B, and can include an electrolyte 5 having an anode electrode 3 over a first surface of the electrolyte 5 and a cathode electrode 7 over a second surface of the electrolyte 5. In one embodiment, a controller 608 may be coupled (wired or wirelessly) to the source 604 and detector 606, as shown in FIG. 6. Controller 608 can be a logic device (e.g., computer) and can include a memory and a processor coupled to the memory, wherein the processor may be configured with processor-executable instructions for performing various functions. In one embodiment, the controller 608 is configured to control the operation of the optical energy source 604 to cause the source 604 to direct optical energy at the fuel cell component 602. In some embodiments, the controller 608 can be configured to control one or more characteristics of the optical energy, such as the power, pulse duration, number or pulses and/or rate (for pulsed radiation) and wavelength of the optical energy directed to component 602. The controller 608 can also be configured to receive an electronic signal representation of the thermal response detected at the detector 606, and to determine the existence of delamination defects in the fuel cell component 602 based on the received thermal response signal.

Figure 7:
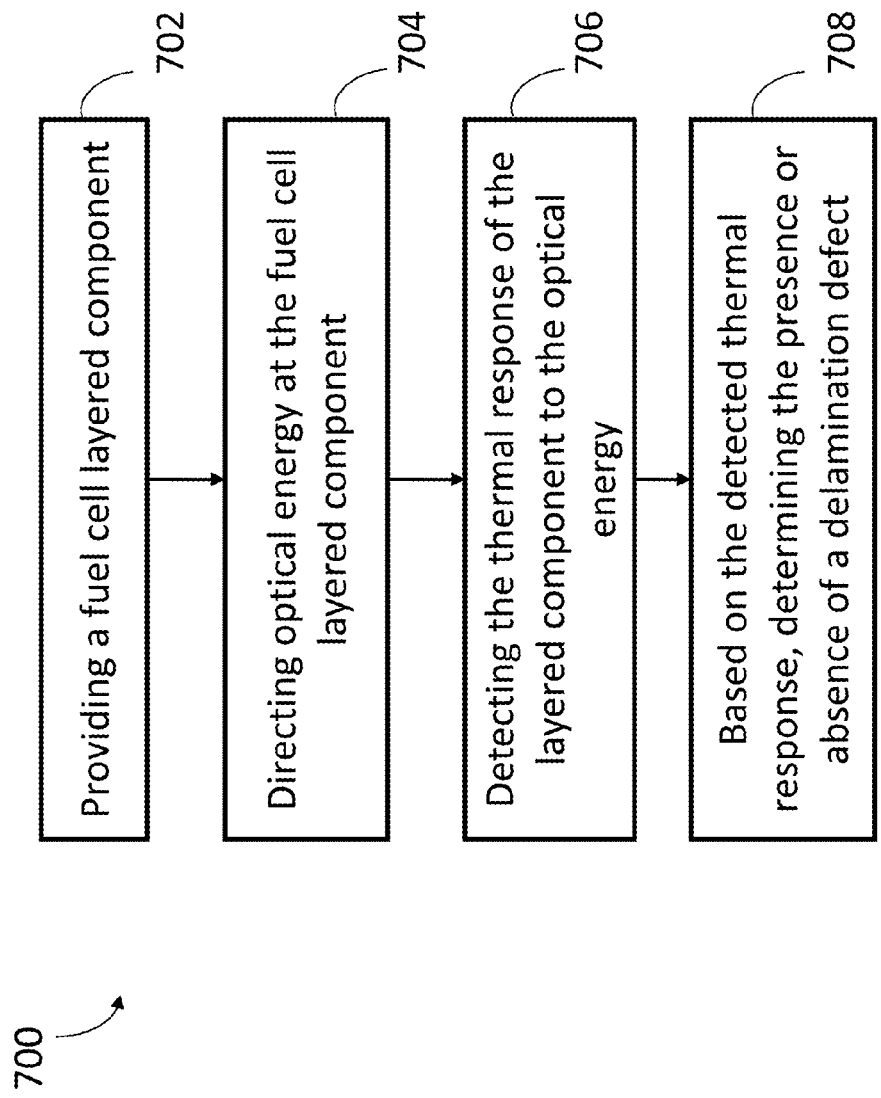
FIG. 7 is a process flow diagram illustrating an embodiment method for detecting a delamination defect in a layered fuel cell component by measuring a thermal energy response of the component to applied optical radiation energy.

FIG. 7 is a process flow diagram illustrating an embodiment method 700 of detecting a delamination defect in a layered component. In step 702, a layered component of a fuel cell is provided. As discussed above, the layered component can be an electrolyte 5 having at least one electrode layer (e.g., an anode electrode 3 and/or a cathode electrode 7) provided on the electrolyte 5. In step 702, optical energy is directed at the layered component. In embodiments, the optical energy can be a flash of high-power broadband light, which can be produced by one or more lamps. The optical energy can be directed to an electrode layer, causing the layer to heat up. In embodiments, the optical energy can provide substantially uniform heat energy over the electrode layer.

In step 704, the thermal response of the layered component is detected. Detecting the thermal response can include detecting changes in the heat pattern of the layered component over time. In various embodiments, the thermal response can be detected with a temperature-sensitive detector, such as an infrared camera. The temperature-sensitive detector can detect changes in the temperature of the layer over short periods of time (e.g., less than 1 second, and generally about 0.1 seconds or less) and preferably includes sufficient temporal and spatial resolution to detect changes in the temperature of different regions of the layer over short periods of time.

Based on the detected thermal response, the presence or absence of a delamination defect can be determined at step 710. In one embodiment, delamination defects can be measured based on changes in the time response of a layer thickness measurement. The thermal diffusion time of the layer can be measured to determine the thickness of the layer. Delaminated electrodes include small air pockets that form between the electrode and the underlying electrolyte material. These air pockets cause heat energy to diffuse more slowly from the delaminated portions of the electrode, making these areas appear much "thicker" than the non-delaminated portions of the layer. These "thicker" portions of the layer can be detected using a high-sensitivity thermal sensor, such as an infrared camera, and can be used to indicate the presence of a delamination defect. In some embodiments, the detected thermal response of the layer can be monitored to identify regions of non-uniform "thickness" in the layer that are indicative of a delamination defect. In some embodiments, the measured "thickness" of the layer (e.g., over portions of the layer or an average thickness over the layer) can be compared with a reference value corresponding to a typical reference component (e.g., a well-sintered, non-delaminated electrode layer on an electrolyte), and the presence or absence of a delamination defect can be determined based on the comparison.

In various embodiments, the method 700 can be used to test a first side of a fuel cell (e.g., anode 3 or cathode 7 side) for delamination defects, and then to test the opposite side of the fuel cell using the same or different testing system. In some embodiments, the testing system 600 can include multiple optical energy sources 604 and thermal sensors 606 which can be positioned on either side of the component 602 for simultaneous testing of the anode 3 and cathode 7 sides of the cell.

Embodiment methods for testing a layered component for delamination defects can take less than about 3 seconds, and more particularly about 1-3 seconds or less, to complete.

In various embodiments, a combined testing method includes testing a fuel cell component for detects using acoustic energy, such as described in connection with FIGS. 3-5, in conjunction with testing the component for defects using optical energy and a thermal sensor, such as described in connection with FIGS. 6-7. The testing methods can be performed in sequence, in any order, and can also be performed simultaneously. In one preferred embodiment, a combined testing method is performed on finished fuel cells, such as SOFCs 1 shown in FIGS. 1 and 2A, in order to identify and eliminate defective cells prior to assembly of a fuel cell stack.

While ceramic electrolytes for a solid oxide fuel cell were described above as the tested objects in certain embodiments, any other electrolytes, or any other ceramic materials not associated with fuel cell systems may also be tested using the above methods. In addition, while layered components including an electrolyte having anode and cathode electrode layers were described above as the tested objects in certain embodiments, any other layered components may also be tested using the above methods.

Further embodiments may include non-destructive methods for testing an interconnect for a fuel cell system to detect cracks in the interconnect. An example of an interconnect 9 for a fuel cell system is illustrated in FIGS. 1A-C. An interconnect 9 may be a chromium-based alloy such as 4-6 wt % Fe and 94-96 wt % Cr, with optionally less than about 1 wt % of Y and unavoidable impurities, and may be formed using a powder metallurgy technique. A protective coating (e.g., a lanthanum strontium manganite (LSM) perovskite coating and/or manganese cobalt oxide spinel coating) may be formed over at least one surface of the interconnect 9, such as over the cathode-facing surface of the interconnect 9.

There are at least two major types of cracks in fuel cell interconnects 9, as illustrated in FIGS. 8A and 8B. A first type of crack 801 extends partially or fully through the thickness of the interconnect (i.e., a through-crack), as shown in FIG. 8A. These through-cracks, which may not be visible to the naked eye, can result in fuel leaks from the anode side to the cathode side of the interconnect 9. Such leaks may cause damage to other layers of the fuel cell stack over time. A second type of crack 803, shown in FIG. 8B, extends generally parallel to the surface of the interconnect 9 (i.e., a lateral crack), and can extend from a flow channel 8 into a rib 10 of the interconnect 9, causing the rib 10 to become raised. This may produce a stress region on the fuel cell adjacent to the raised rib 10, significantly increasing the probability that the fragile fuel cell will crack. Both types of cracks are difficult to detect using conventional techniques. Thus, it would be desirable to provide a rapid and accurate technique for detecting cracks in interconnects, including both through-cracks and lateral cracks, before the interconnects are incorporated into a fuel cell stack.

Various embodiments may include non-destructive methods for detecting cracks in an interconnect by active thermography. The interconnect may be stimulated by one or more types of energy, such as ultrasound, induction (i.e., inductive heating), or optical energy (e.g., ultraviolet, visible, and/or infrared radiation), and the thermal response of the fuel cell component may be observed. Cracks in the interconnect may be detected based on irregularities in the observed thermal response.

Figure 9:
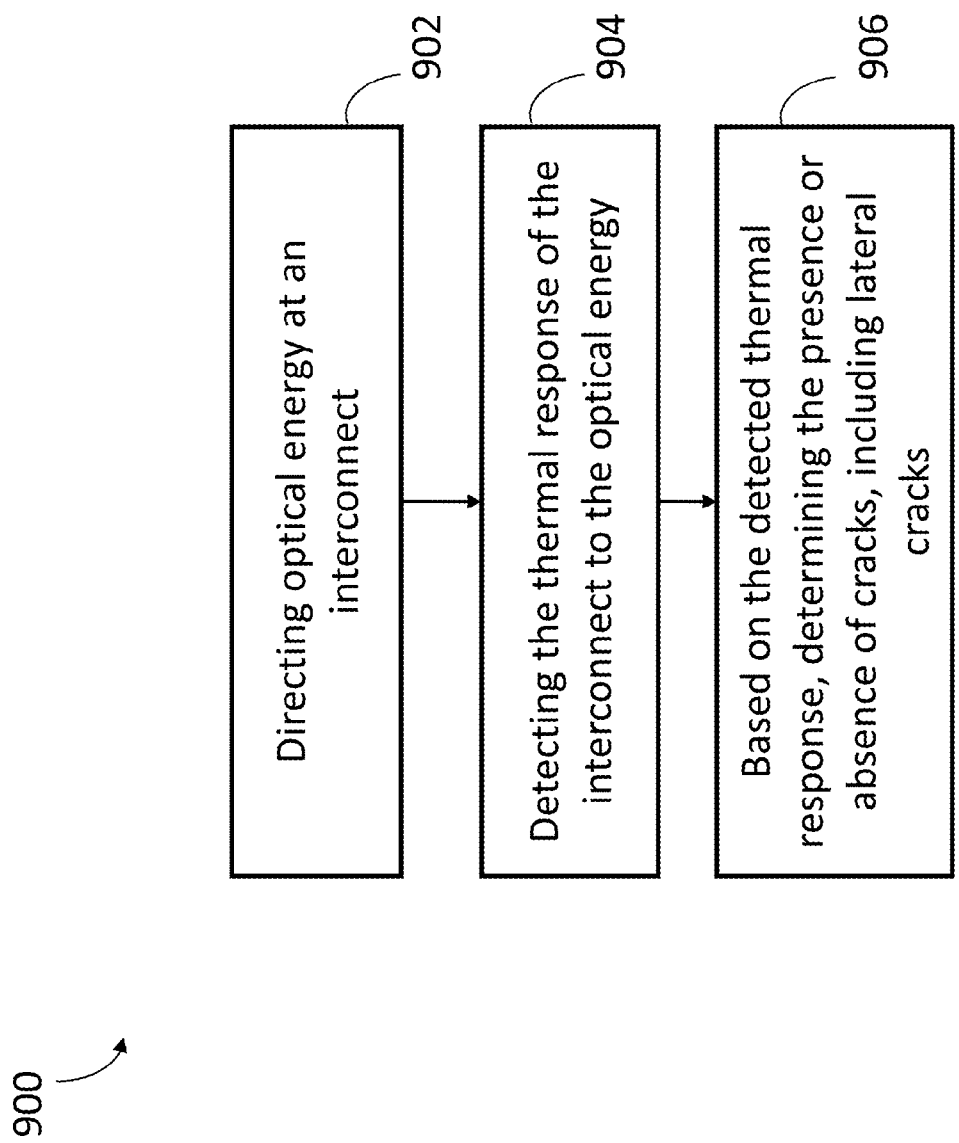
FIG. 9 is a process flow diagram illustrating an embodiment method for detecting a crack defect in an interconnect by measuring a thermal energy response of the interconnect to applied optical radiation energy.

FIG. 9 is a process flow diagram illustrating an embodiment method 900 of detecting a crack in an interconnect of a fuel cell, such as interconnect 9 shown in FIGS. 1A-C. The method 900 may be performed using an active thermography system 600 such as shown in FIG. 6, that includes a source 604 configured to direct optical radiation energy (e.g., ultraviolet, visible or infrared radiation, preferably infrared radiation) at an interconnect, and a detector 606 (e.g., an infrared camera or infrared photodetector), for detecting a thermal response of the interconnect.

In step 902, optical energy is directed at the interconnect. In embodiments, the optical energy can be a flash of high-power broadband light, which can be produced by one or more lamps. The optical energy can be directed to a surface of the interconnect, causing the interconnect to heat up. In embodiments, the optical energy can provide substantially uniform heat energy over the surface of the interconnect.

In step 904, the thermal response of the interconnect is detected. Detecting the thermal response can include detecting changes in the heat pattern of the interconnect over time. In various embodiments, the thermal response can be detected with a temperature-sensitive detector, such as an infrared camera. The temperature-sensitive detector can detect changes in the temperature of the interconnect over short periods of time (e.g., less than 1 second, and generally about 0.1 seconds or less) and preferably includes sufficient temporal and spatial resolution to detect changes in the temperature of different regions of the interconnect over short periods of time.

Based on the detected thermal response, the presence or absence of a crack can be determined at step 906. In particular, an active thermography measurement technique using optical irradiation may be used to detect for the presence of lateral cracks in the interconnect, such as crack 803 illustrated schematically in FIG. 8B. In one embodiment, a crack in the interconnect can be measured based on changes in the thermal response of the interconnect, or of portions thereof. A thermal diffusion time can be measured for all or portions of an interconnect. An interconnect with a lateral crack 803 may include small air pockets that form between within or beneath the rib(s) 10 through which the crack extends. These air pockets cause heat energy to diffuse more slowly from the cracked portions of the interconnect, making these areas appear much "thicker" than the non-cracked portions of the interconnect (i.e., uncracked ribs). These "thicker" portions of the interconnect can be detected using a high-sensitivity thermal sensor, such as an infrared camera, and can be used to indicate the presence of a crack. In some embodiments, the detected thermal response of the interconnect can be monitored to identify regions of non-uniform "thickness" in the interconnect that are indicative of a lateral crack. In some embodiments, the measured thermal response of the interconnect (e.g., over portions of the interconnect or an average thickness over the interconnect) can be compared with a reference value corresponding to a typical reference component (e.g., an interconnect known not to have cracks), and the presence or absence of a crack can be determined based on the comparison.

Preferably, the IR thermography with the optical radiation source comprises IR lock-in thermography in which the optical radiation is periodically modulated and the interconnect thermal response is then correlated and averaged over many periods. However, the IR thermography may be of the non-lock-in type.

For example, as described in an article by S. Huth, et al., "Lock-in IR-Thermography—a novel tool for material and device characterization", available at http://www.mpi-halle.mpg.de/mpi/publi/pdf/540_02.pdf, lock-in thermography uses the lock-in principle which involves periodically modulating heat (e.g., the optical radiation) into an object (e.g., the interconnect) and monitoring only the periodic surface temperature modulation phase-referred to the modulated heat supply. Hence, if the surface temperature is measured via an infrared (IR) thermocamera, lock-in thermography means that the information of each pixel of the image is processed as if it were fed into a lock-in amplifier. As described by Huth, et al., the digital lock-in correlation procedure includes successively multiplying the incoming IR images by a set of weighting factors and summing up the results in a frame storage. The weighting factors are approximating a harmonic function and are synchronized to the pulsed bias applied to the sample. Since amplitude and phase of the measured surface temperature modulation may change with position, a two-phase lock-in correlation has to be used. Thus, a lock-in thermography measurement can yield either an amplitude and a phase image, or an in-phase (0°) and a quadrature (−90°) image, referring to the phase of the periodic heat supply. Other types of lock-in thermography can also be used.

In various embodiments, the method 900 can be used to test a first side of an interconnect, and then to test the opposite side of the interconnect using the same or different testing system. In some embodiments, the testing system 600 can include multiple optical energy sources 604 and thermal sensors 606 which can be positioned on either side of an interconnect (such as interconnect 9, shown in FIGS. 1A-C) for simultaneous testing of the anode- and cathode-facing sides of the interconnect.

Embodiment methods for testing an interconnect for cracks using an optical excitation active thermography technique can take less than about 3 seconds, and more particularly about 1-2 seconds or less, to complete.

An active thermography technique using an optical radiation (e.g., flashlamp) excitation source may also be used to detect the thickness of a protective coating (e.g., a lanthanum strontium manganite (LSM) perovskite coating and/or manganese cobalt oxide spinel coating) over at least one surface of an interconnect 9, such as over the cathode-facing surface of the interconnect 9. A high-sensitivity detector, such as an infrared camera, may measure the thermal diffusion time of the coating to detect for coating defects, such as non-uniform thickness, void areas, and/or coatings that are too thick or too thin compared to known good coating layers.

Figure 10:
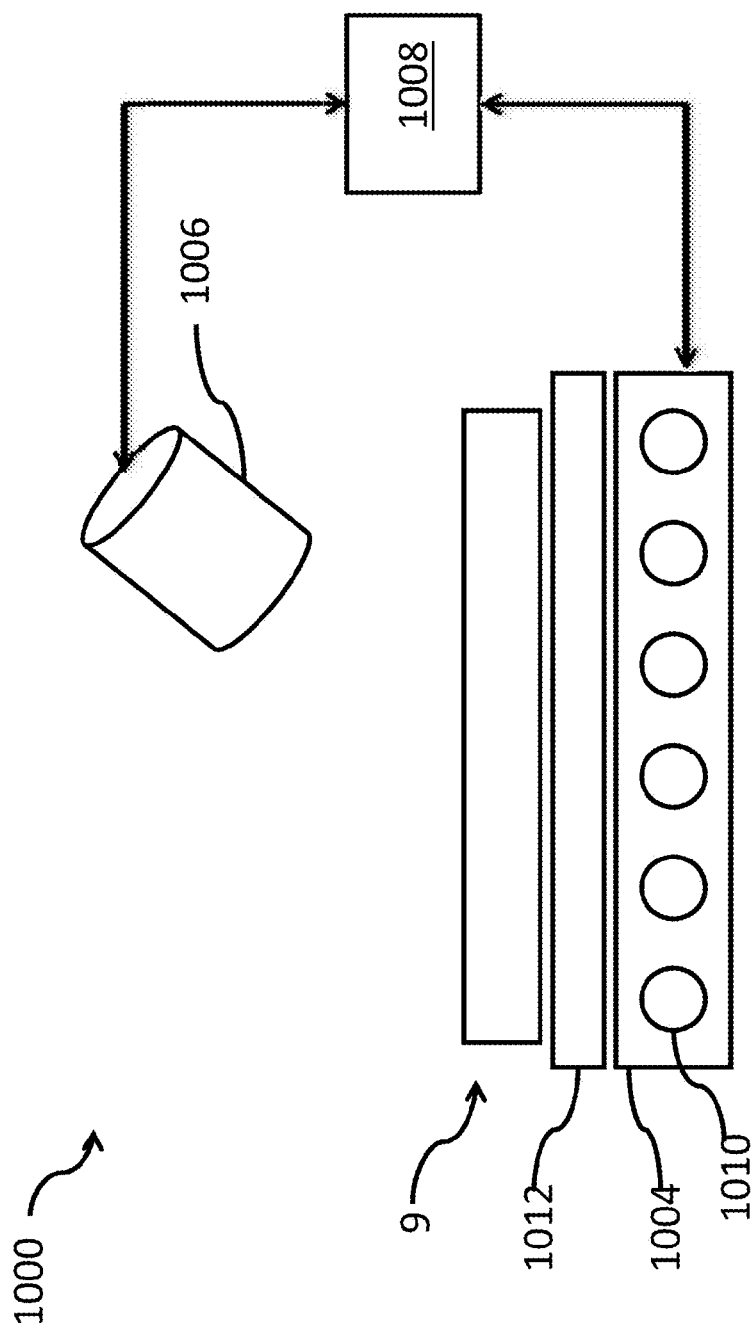
FIG. 10 illustrates an interconnect and a testing apparatus for detecting a crack defect in the interconnect by measuring a thermal response of the interconnect to inductive excitation.

Further embodiments may include non-destructive testing for cracks in an interconnect by active thermography using stimulation from an inductance coil. Inductance coils may vary in shape and power. FIG. 10 illustrates an example test setup 1000 using a liquid cooled manifold 1004 containing rectangular inductance excitation source (i.e., coil) 1010. A cross section of the rectangular inductance coil 1010 is shown in FIG. 10 with the coil coming out of the page such that the rectangular coil appears as circles rather than a rectangle. Alternate embodiments may rely on various shapes of inductance coils, such as a circular (i.e., spiral with a roughly circular outer diameter) inductive coil. A stage 1012, such as a wooden (or another material which is not inductively heated) stage not heated by inductive heating, may support the interconnect 9. A radiation detector 1006, such as an infrared camera, may be positioned over a surface of the interconnect 9, opposite the inductance excitation source 1010, to detect a thermal response of the interconnect 9.

A controller 1008 may be coupled (wired or wirelessly) to the inductance excitation source 1010 and detector 1006, as shown in FIG. 10. Controller 1008 can be a logic device (e.g., computer) and can include a memory and a processor coupled to the memory, wherein the processor may be configured with processor-executable instructions for performing various functions. In one embodiment, the controller 1008 is configured to control the operation of the inductance excitation source 1010 to cause the source 1010 to inductively stimulate the interconnect 9, causing the interconnect to heat up. The controller 1008 can also be configured to receive an electronic signal representation of the thermal response detected at the detector 1006, and to determine the existence of defects in the interconnect 9 based on the received thermal response signal.

Figure 11:
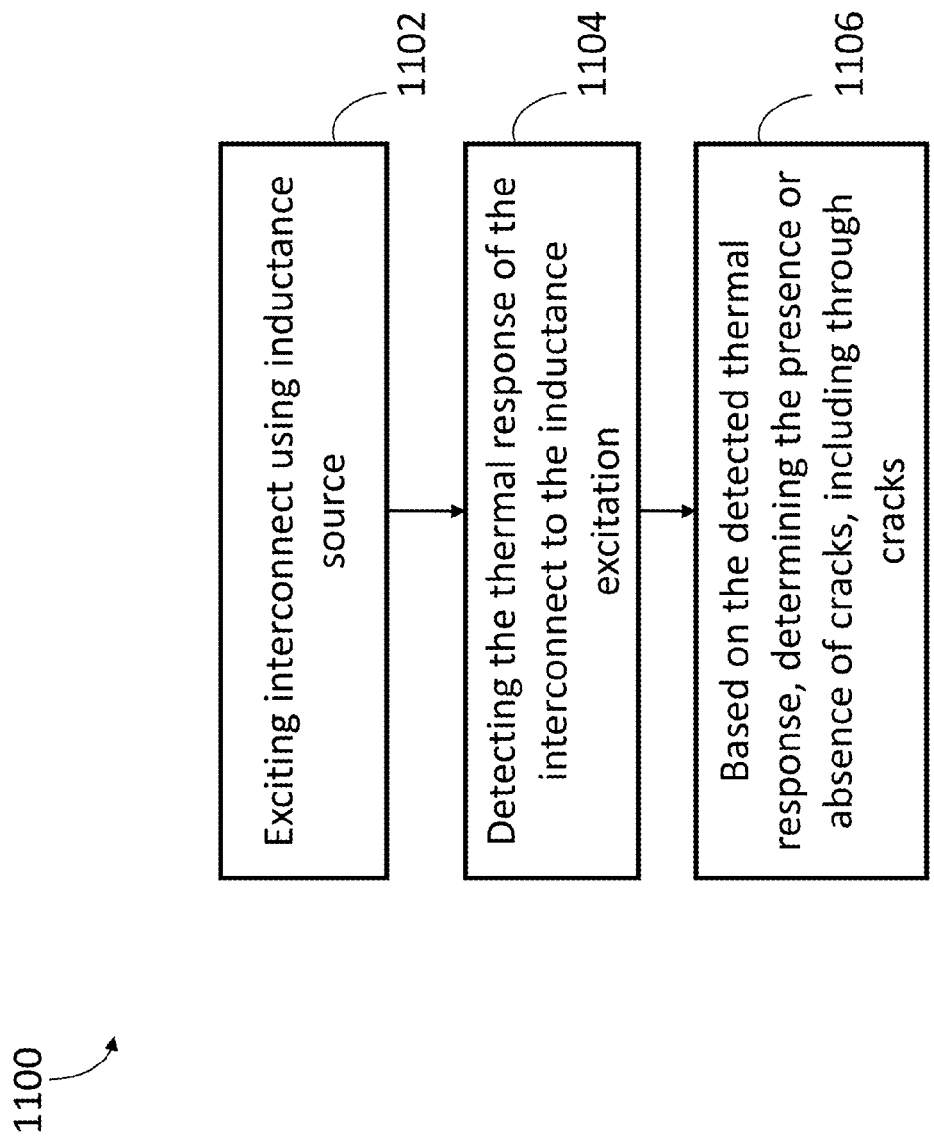
FIG. 11 is a process flow diagram illustrating an embodiment method for detecting a crack defect in an interconnect by measuring a thermal energy response of the interconnect to stimulation from an inductance excitation source.

FIG. 11 is a process flow diagram illustrating an embodiment method 1100 of detecting a crack in an interconnect of a fuel cell, such as interconnect 9 shown in FIGS. 1A-C. The method 1100 may be performed using an active thermography system 1000 such as shown in FIG. 10, that includes an induction excitation source 1010 configured to inductively stimulate an interconnect, and a detector 1006 (e.g., an infrared camera or infrared photodetector), for detecting a thermal response of the interconnect.

In step 1102, the interconnect is excited using an induction excitation source, causing the interconnect to heat up. In step 1104, the thermal response of the interconnect is detected. Detecting the thermal response can include detecting changes in the heat pattern of the interconnect over time. In various embodiments, the thermal response can be detected with a temperature-sensitive detector, such as an infrared camera. The temperature-sensitive detector can detect changes in the temperature of the interconnect over short periods of time (e.g., less than 1 second, and generally about 0.1 seconds or less) and preferably includes sufficient temporal and spatial resolution to detect changes in the temperature of different regions of the interconnect over short periods of time.

Based on the detected thermal response, the presence or absence of a crack can be determined at step 1006. In particular, an active thermography measurement technique using inductance stimulation (i.e., heating) may be used to detect for the presence of through cracks in the interconnect, such as crack 801 illustrated schematically in FIG. 8A. Preferably, non-modulated induction excitation is used in a non-lock-in type IR thermography.

In one embodiment, a crack in the interconnect can be measured based on changes in the thermal response of the interconnect, or of portions thereof. An inductive excitation source may produce generally uniform heating through the thickness of an interconnect. An interconnect with a through crack may include small void areas or air pockets extending through the thickness of the interconnect that produce localized areas of non-uniform inductive heating and/or thermal diffusion. These cracked region(s) of the interconnect can be detected using a high-sensitivity thermal sensor, such as an infrared camera, and can be used to indicate the presence of a through crack. In some embodiments, the detected thermal response of the interconnect can be monitored to identify regions of non-uniform heating or diffusion in the interconnect that are indicative of a through crack. In some embodiments, the measured thermal response of the interconnect (e.g., over portions of the interconnect) can be compared with a reference value corresponding to a typical reference component (e.g., an interconnect known not to have cracks), and the presence or absence of a crack can be determined based on the comparison.

Embodiment methods for testing an interconnect for cracks using an inductive excitation active thermography technique can take less than about 3 seconds, and more particularly about 1-2 seconds or less, to complete.

Further embodiments may include non-destructive testing of interconnects using active thermography that includes multiple stimulations of the interconnect using different excitation sources, such as an optical radiation source and an inductive excitation source, detecting the thermal response of the interconnect from each of the stimulations by the multiple excitation sources, and determining the existence of defects in the interconnect based on the detected thermal responses. In one example, a stimulation from an optical radiation source (e.g., a flashlamp) may be used to detect a first defect or set of defects (e.g., lateral cracks, protective coating defects, etc.) and stimulation from an inductive excitation source may be used to detect a second defect or set of defects (e.g., through cracks).

Figure 12:
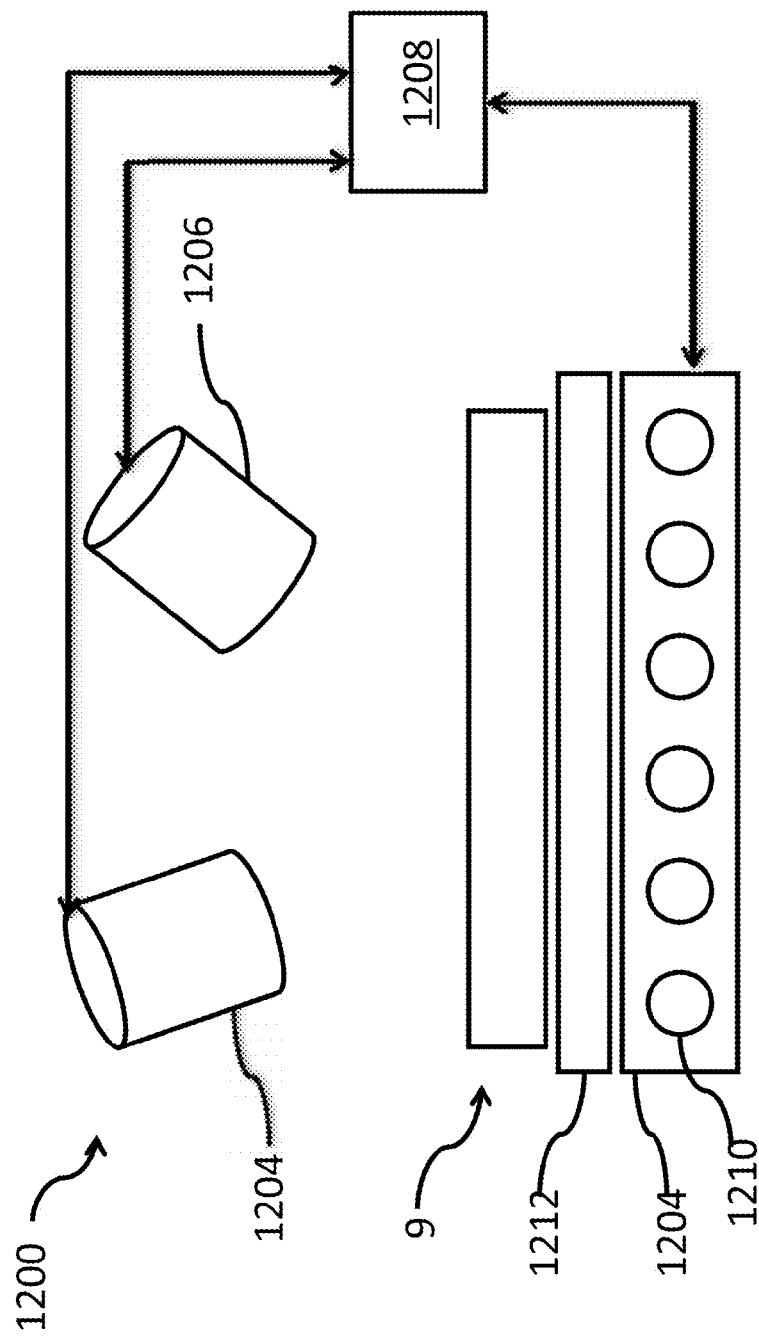
FIG. 12 illustrates an interconnect and a testing apparatus for detecting crack defects in the interconnect by measuring the thermal response of the interconnect to excitation by both optical radiation and inductive stimulation.

FIG. 12 illustrates a system 1200 for multi-modal active thermography testing of a fuel cell component, such as an interconnect 9. The system 1200 in this embodiment includes an inductance excitation source (i.e., coil) 1210, which may be contained in a liquid cooled manifold 1204, and an optical radiation excitation source 1204 (e.g., a flashlamp, halogen lamp, LED, laser source, etc.). An interconnect 9 may be positioned on a support 1012, which is preferably made of a material that is not inductively heated. In the embodiment of FIG. 12, a single radiation detector 1206 is positioned to detect the thermal response of the interconnect 9 in response to excitation from inductance source 1210 and optical radiation source 1204. A controller 1208 controls the operation of the excitation sources 1210, 1204 and detector 1206 and may be operable to cause the excitation sources 1210, 1204 to sequentially excite the interconnect 9 (i.e., excitation by inductive source 1210 followed by excitation by optical radiation source 1204, or vice versa). The detector 1206 may detect the thermal response of the interconnect 9 following each excitation. The controller 1208 may be configured to receive an electronic signal representation of each of the thermal responses detected at the detector 1206, and to determine the existence of defects in the interconnect 9 based on the received thermal response signal. The thermal response from the optical radiation excitation may be used to detect a first defect or set of defects (e.g., lateral cracks, protective coating defects, etc.) and the thermal response from the inductive excitation may be used to detect a second defect or set of defects (e.g., through cracks).

In an alternative embodiment, the system 1200 may include multiple detectors 1206 for detecting the thermal response from each excitation source 1210, 1204. For example, the interconnect 9 may move on a belt or other movable support from a first testing station, which may include an inductive excitation source and associated detector, to a second testing station, which may include an optical radiation excitation source and associated detector. The order of the testing may be reversed. In embodiments, the interconnect 9 may remain stationary, and the excitation source(s) and associated detectors may move relative to the interconnect.

In various embodiments, at least the optical radiation excitation of the interconnect may be performed on two sides of the interconnect, such as a cathode-facing side and an anode-facing side. In embodiments, the interconnect may be provided in the testing apparatus with a first side facing the optical radiation source 1204 and detector 1206, and then may be turned over to repeat at least the optical radiation excitation test on the second side of the interconnect. In other embodiments, a second optical radiation source 1204 and detector 1206 pair may be provided to perform the test on the second side of the interconnect.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method for testing a fuel cell component, comprising:
   directing acoustic energy into the component, wherein directing acoustic energy comprises stimulating the component at a resonance frequency of the component;
   detecting acoustic energy from the component, wherein detecting the acoustic energy comprises detecting a resonance response of the component;
   analyzing a characteristic of the detected acoustic energy, wherein analyzing a characteristic comprises measuring a damping of an amplitude of the detected resonance response; and
   based on the analyzing, determining a presence or absence of a defect in the component, which comprises determining the presence of a defect when a measured damping value exceeds a pre-determined maximum damping deviation value from a reference value.

2. A method for testing a fuel cell component, comprising:
   directing acoustic energy into the component, wherein directing acoustic energy comprises stimulating the component at a resonance frequency of the component;
   detecting acoustic energy from the component, wherein detecting the acoustic energy comprises detecting a resonance response of the component;
   analyzing a characteristic of the detected acoustic energy, wherein analyzing a characteristic comprises measuring a damping of an amplitude of the detected resonance response; and
   based on the analyzing, determining a presence or absence of a defect in the component, which comprises determining the presence of a defect when a measured resonance peak shift value exceeds a pre-determined maximum shift deviation value.

* * * * *